US006890517B2

(12) United States Patent
Drechsel et al.

(10) Patent No.: US 6,890,517 B2
(45) Date of Patent: May 10, 2005

(54) INHALABLE FORMULATION OF A SOLUTION CONTAINING A TIOTROPIUM SALT

(75) Inventors: Karin Drechsel, Mannheim (DE); Barbara Niklaus-Humke, Damscheid (DE); Christel Schmelzer, Ingelheim (DE); Petra Barth, Mainz (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/395,777

(22) Filed: Mar. 24, 2003

(65) Prior Publication Data

US 2003/0181478 A1 Sep. 25, 2003

Related U.S. Application Data

(63) Continuation of application No. 10/040,196, filed on Oct. 25, 2001, now abandoned.
(60) Provisional application No. 60/253,613, filed on Nov. 28, 2000.

(30) Foreign Application Priority Data

Oct. 31, 2000  (DE) .......................................... 100 54 042

(51) Int. Cl.$^7$ ............................ A61K 9/14; A61K 38/00
(52) U.S. Cl. ........................ 424/45; 424/400; 514/826; 514/217.05; 514/291; 514/171; 239/333; 128/200.14
(58) Field of Search ............................ 424/45, 46, 400; 514/826, 217.05, 291, 171; 239/333; 128/200.14

(56) References Cited

U.S. PATENT DOCUMENTS

| | | | |
|---|---|---|---|
| 4,042,700 A | 8/1977 | Banholzer et al. | |
| 4,608,377 A | 8/1986 | Banholzer et al. | |
| 4,783,534 A | 11/1988 | Banholzer et al. | |
| 5,610,163 A | 3/1997 | Banholzer et al. | |
| 5,654,314 A | 8/1997 | Banholzer et al. | |
| 5,770,738 A | 6/1998 | Banholzer et al. | |
| 5,824,669 A | 10/1998 | Garvey et al. | |
| 5,952,505 A | 9/1999 | Banholzer et al. | |
| 5,964,416 A * | 10/1999 | Jaeger et al. | ................ 239/333 |
| 6,433,027 B1 * | 8/2002 | Bozung et al. | ............. 514/291 |
| 6,486,321 B2 | 11/2002 | Banholzer et al. | |
| 6,506,900 B1 | 1/2003 | Banholzer et al. | |
| 2001/0008632 A1 * | 7/2001 | Freund et al. | ............... 424/400 |
| 2002/0111363 A1 | 8/2002 | Drechsel et al. | |
| 2002/0151541 A1 | 10/2002 | Pairet et al. | |
| 2002/0183292 A1 | 12/2002 | Pairet et al. | |
| 2003/0018019 A1 | 1/2003 | Meade et al. | |
| 2003/0066524 A1 * | 4/2003 | Hochrainer et al. | ... 128/200.14 |

FOREIGN PATENT DOCUMENTS

| | | |
|---|---|---|
| DE | 42 03 306 A1 | 8/1993 |
| DE | 19921693 | 7/1997 |
| DE | 19825027 | 6/1998 |
| DE | 19653969 | 11/2000 |
| EP | 0504112 | 9/1992 |
| WO | WO 97/46243 | 12/1997 |
| WO | WO 98/27959 A2 | 7/1998 |
| WO | WO 00/07567 | 2/2000 |
| WO | WO 00/23037 A1 | 4/2000 |
| WO | WO00/47200 A1 | 8/2000 |

OTHER PUBLICATIONS

Mon, F. et al; Aerosol Therapy In Asthma, Revue Des Maladies Respiratoires, vol. 6., No. 3, 1989, pp. 189–200.

Balzano, G. et al; Effectiveness and Acceptability of a domicillary multidrug inhalation treatment in elderly patients with chronic airflow obstruction; Journal of Aerosol Medicine, The Official Journal of the Int'l. Society for Aerosol in Medicine U.S. 2000 Spring, vol. 13, No. 1 Apr. 2000 (pp. 25–33).

Rutgers S.R. et al; Short Term Treatment with Budesonide does not improve hyperresponsiveness to adenosine 5'monophosphate in COPD, American Journal of Respiratory and Critical Care Medicine, U.S., Mar. 1998, vol. 157, No. 3 Pt. 1,Mar. 1998 pp. 880–886.

Van Schayck, C.P., et al; Periodic treatment regimens with inhaled steroids in asthma or chronic obstructive pulmonary disease. Is it possible? Journal of American Medical Association. U.S. Jul. 12, 1995, vol. 278, No. 2, Jul. 12, 1995 (1995–07) pp. 151–164.

Naclerio, R.M.; Optimizing treatment options., Clinical and Experimental Allergy, vol. 28., No. Suppl. 6, Dec. 1998 pp. 54–59.

(Continued)

Primary Examiner—Gary Kunz
Assistant Examiner—Mina Haghighatian
(74) Attorney, Agent, or Firm—Michael P. Morris; Mary-Ellen M. Devlin; Andrea D. Small (57) ABSTRACT

A liquid, propellant-free pharmaceutical preparation comprising:
 (a) a first active substance comprising a tiotropium salt, in a concentration based on tiotropium of between 0.0005% and 5% by weight;
 (b) a second active substance selected from the group consisting of: an antiallergic, antihistamine, steroid, and leukotriene antagonist;
 (c) a solvent selected from water or a water/ethanol mixture; and
 (d) a pharmacologically acceptable preservative,
 wherein the pH of the preparation is adjusted to between 2.0 and 4.5 with an acid and the tiotropium salt is dissolved in the solvent,
 optionally including a pharmacologically acceptable complexing agent, stabilizer, a pharmacologically acceptable cosolvent, or other pharmacologically acceptable adjuvants and additives; a method for administering a pharmaceutical preparation by nebulizing the pharmaceutical preparation in an inhaler, and a method of treating asthma or COPD in a patient using the pharmaceutical preparation.

81 Claims, 2 Drawing Sheets

OTHER PUBLICATIONS

Nishimura, K. et al.; Additive effect of Oxitroplum bromide in combination with inhaled corticosteroids in the treatment of elderly patients with chronic asthma. Allergology Int'l. vol. 48, No. 1, Mar. 1999.

Pavia, D. et al; Preliminary data from phase II studies with Resplmat, a propellant–free soft mist inhaler, Journal of Aerosol Medicine, The Offical Journal of the Int'l. Society for Aerosols in Medicine U.S. 1999, vol. 12 Suppl 1, 1999, pp. S33–S39.

Patent Abstract of Japan, vol. 1999, No. 2, Feb. 26, 1999 & JP 10 298107A (Taisho Pharmaceutical Co. Ltd) Nov. 10, 1998 Abstract.

English Abstract for DE 42 03 306 A1.

* cited by examiner

INHALABLE FORMULATION OF A SOLUTION CONTAINING A TIOTROPIUM SALT

RELATED APPLICATIONS

This is a continuation of U.S. Ser. No. 10/040,196, filed Oct. 25, 2001, now abandoned, which claimed benefit under 35 U.S.C. § 119(e) of prior provisional application Serial No. 60/253,613, filed Nov. 28, 2000.

BACKGROUND OF THE INVENTION

The present invention relates to a propellant-free inhalable formulation of a pharmaceutically acceptable salt of tiotropium dissolved in water or a mixture of water and ethanol, in conjunction with at least one other active substance preferably administered by inhalation, and propellant-free inhalable aerosols resulting therefrom. The formulation according to the invention is particularly suitable for administering the active substance by inhalation, especially for treating asthma and chronic obstructive pulmonary disease (COPD).

Tiotropium, chemically (1α, 2β, 4β, 5α,7β)-7-[(hydroxydi-2-thienylacetyl)oxy]-9,9-dimethyl-3-oxa-9-azoniatricyclo[3.3.1.0$^{2,4}$]nonane, is known as tiotropium bromide from European Patent Application EP 418 716 A1. The bromide salt of tiotropium has the following chemical structure:

(I)

The compound has valuable pharmacological properties and is known by the name tiotropium bromide. Tiotropium and its salts are highly effective anticholinergics and can provide therapeutic benefit in the treatment of asthma or COPD (chronic obstructive pulmonary disease). The monohydrate of tiotropium bromide is also pharmacologically valuable. Both compounds are a preferred object of the present invention.

SUMMARY OF THE INVENTION

The present invention relates to liquid active substance formulations of these compounds which can be administered by inhalation; the liquid formulations according to the invention have to meet high quality standards.

DESCRIPTION OF THE DRAWINGS

FIGS. 1a and 1b herein are identical to FIGS. 6a and 6b of WO 97/12687.

DETAILED DESCRIPTION OF THE INVENTION

To achieve an optimum distribution of active substances in the lung, it makes sense to use a liquid formulation without propellant gases administered using suitable inhalers. Those inhalers which are capable of nebulizing a small amount of a liquid formulation in the dosage needed for therapeutic purposes within a few seconds into an aerosol suitable for therapeutic inhalation are particularly suitable. Within the scope of the invention, preferred nebulizers are those in which an amount of less than 100 microliters, preferably less than 50 microliters, most preferably less than 20 microliters of active substance solution can be nebulized preferably in one puff to form an aerosol having an average particle size of less than 20 microns, preferably less than 10 microns, so that the inhalable part of the aerosol already corresponds to the therapeutically effective quantity.

Figure 1A:
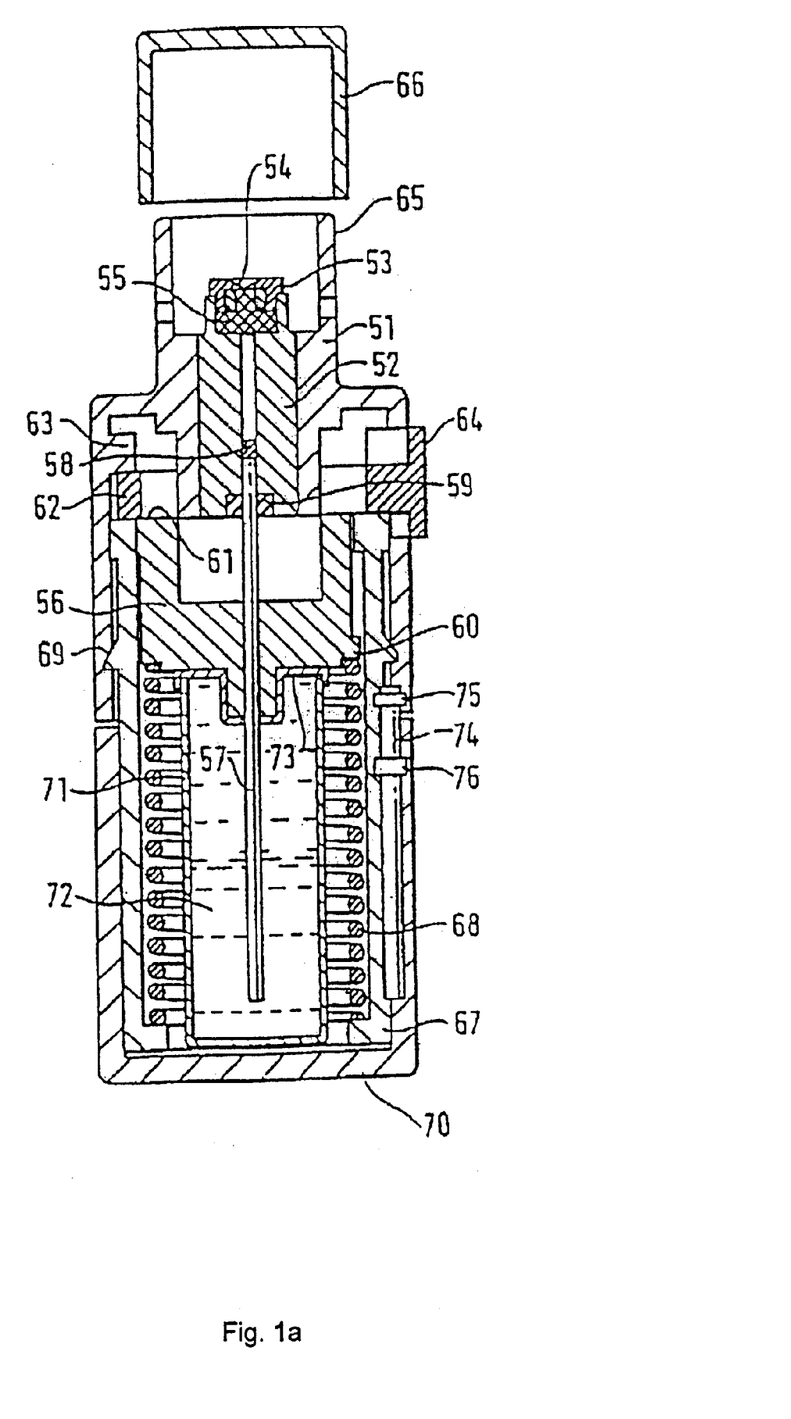
FIG. 1a shows a longitudinal section of the RESPIMAT® nebulizer disclosed in WO 97/12687 through the atomizer with the spring under tension.
Figure 1B:
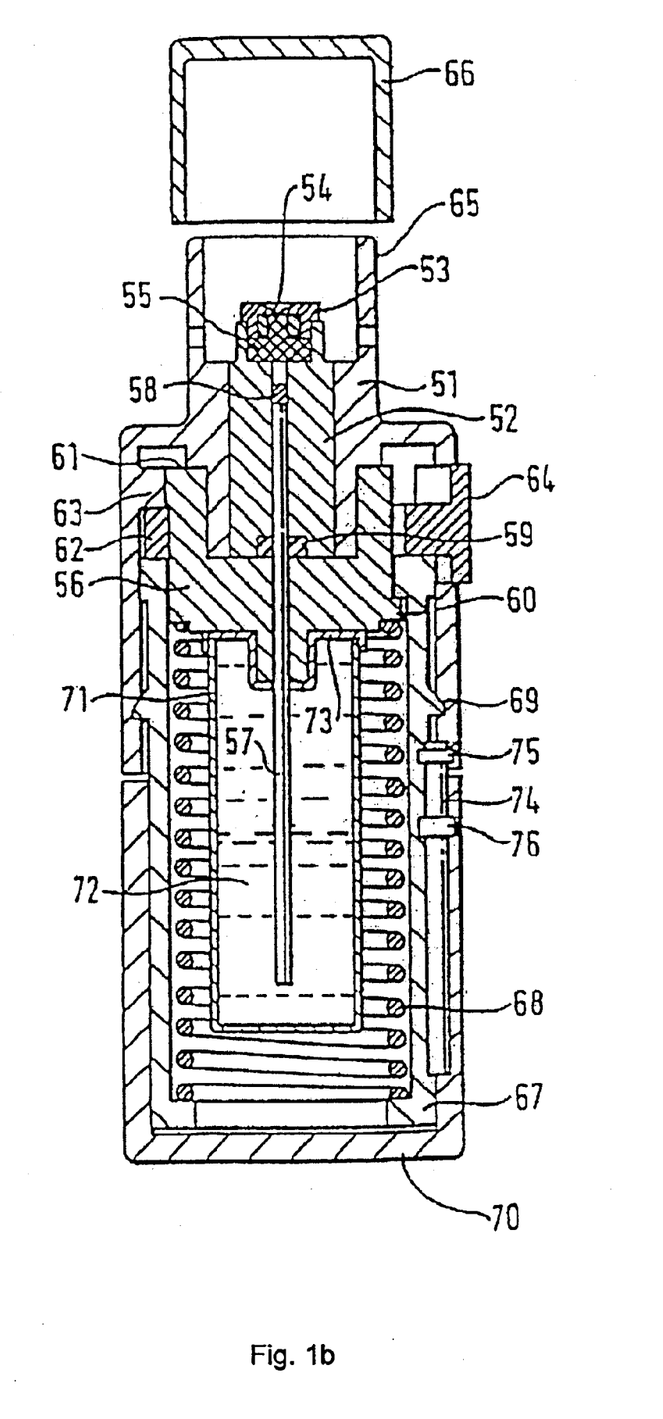
FIG. 1b shows a longitudinal section of the RESPIMAT® nebulizer disclosed in WO 97/12687 through the atomizer with the spring released.

An apparatus of this kind for the propellant-free administration of a metered amount of a liquid pharmaceutical composition for inhalation is described in detail, for example, in International Patent Application WO 91/14468 "Atomizing Device and Methods" and also in WO 97/12687, cf FIGS. 6a and 6b and the accompanying description. In a nebulizer of this kind a pharmaceutical solution is converted by means of a high pressure of up to 500 bar into an aerosol destined for the lungs, which is sprayed. Within the scope of the present specification reference is expressly made to the entire contents of the literature mentioned above.

In inhalers of this kind, the formulations of solutions are stored in a reservoir. It is essential that the active substance formulations used are sufficiently stable when stored and at the same time are such that they can be administered directly, if possible without any further handling, in accordance with their medical purpose. Moreover, they must not contain any ingredients which might interact with the inhaler in such a way as to damage the inhaler or the pharmaceutical quality of the solution or of the aerosol produced.

To nebulize the solution, a special nozzle is used as described, for example, in WO 94/07607 or WO 99/16530, reference is expressly made here to both these publications and each of which is incorporated herein by reference in their entireties.

WO 98/27959 discloses formulations of solutions for the inhaler described above which contain as additive the disodium salt of edetic acid (sodium edetate). For aqueous formulations of solutions which are to be converted into inhalable aerosols using the inhaler described above, the specification favors a minimum concentration of sodium edetate of 50 mg/100 ml, in order to reduce the incidence of spray anomalies. Among the Examples disclosed there is a formulation containing tiotropium bromide. In this formulation, the active substance is dissolved in water. The proportion of sodium edetate is again 50 mg/100 ml.

Surprisingly, it has now been found that formulations of solutions of tiotropium salts in water or a water-ethanol mixture wherein the proportion of the additive sodium edetate is significantly less than 50 mg/100 ml show a reduction in the scattering of the composition delivered, compared with the formulation containing tiotropium bromide known from the prior art. In addition, the spray quality is very good. The resulting aerosol has very good properties for administration by inhalation.

Another advantage of the formulation is that, thanks to the absence of or reduction in the additive sodium edetate in the active substance formulation, the pH of the solution formulation can be lowered. Low pH levels are necessary for the long-term stability of the tiotropium salts in the formulation.

It is therefore an aim of the present invention to provide an aqueous active substance formulation containing a pharmaceutically acceptable tiotropium salt which meets the high standards needed in order to be able to achieve optimum nebulization of a solution using the inhalers mentioned hereinbefore. The active substance formulations according to the invention must be of sufficiently high pharmaceutical quality, i.e., they should be pharmaceutically stable over a storage time of some years, preferably at least one year, more preferably two years.

Another aim is to provide propellant-free formulations of solutions containing tiotropium salts which are nebulized under pressure using an inhaler, the composition delivered by the aerosol produced falling reproducibly within a specified range.

Another aim is to provide formulations of solutions with tiotropium and another active substance which can be administered by inhalation.

According to the invention, any pharmaceutically acceptable salts of tiotropium may be used for the formulation. When the term tiotropium salt is used within the scope of the present invention, this is to be taken as a reference to tiotropium. According to the invention a reference to tiotropium, which is the free ammonium cation, corresponds to a reference to tiotropium in the form of a salt (tiotropium salt) which contains an anion as counter-ion. Tiotropium salts which may be used within the scope of the present invention are preferably compounds which contain, in addition to tiotropium as counter-ion (anion), chloride, bromide, iodide, methanesulfonate, p-toluenesulfonate, and/or methylsulfate.

Within the scope of the present invention tiotropium bromide is preferred as the salt. References to tiotropium bromide within the scope of the present invention must always be taken as references to all possible amorphous and crystalline modifications of tiotropium bromide. These may for example contain molecules of solvent in their crystalline structure. Of all the crystalline modifications of tiotropium bromide those which also contain water (hydrates) are preferred according to the invention. It is particularly preferred within the scope of the present invention to use tiotropium bromide monohydrate.

In the formulations according to the invention combinations with a tiotropium salt and only one other active substance are preferred.

In the formulations according to the invention, the tiotropium salts are dissolved in a solvent. The solvent may be exclusively water, or it may be a mixture of water and ethanol. Ethanol may be added to the formulation in order to increase the solubility of additives or other active substances apart from the tiotropium salt, preferably tiotropium bromide or tiotropium bromide monohydrate. The relative proportion of ethanol to water is not limited; it may be 90% by volume, for example. Preferably, the maximum limit of ethanol is 70% by volume, particularly 60% by volume and most preferably 30% by volume. The remaining % by volume consist of water. The preferred solvent is water without the addition of ethanol.

The concentration of the tiotropium salt based on the proportion of tiotropium in the finished pharmaceutical preparation depends on the therapeutic effect sought. For most of the complaints which respond to tiotropium the concentration of tiotropium is between 0.0005% and 5% by weight, preferably between 0.001% and 3% by weight.

The pH of the formulation according to the invention is between 2.0 and 4.5, preferably between 2.5 and 3.5 and more preferably between 2.7 and 3.5 and particularly preferably between 2.7 and 3.2. Most preferred are pHs with an upper limit of 3.1.

The pH is adjusted by the addition of pharmacologically acceptable acids.

Examples of inorganic acids which are preferred for this purpose include: hydrochloric acid, hydrobromic acid, nitric acid, sulfuric acid, and/or phosphoric acid.

Examples of particularly suitable organic acids are: ascorbic acid, citric acid, malic acid, tartaric acid, maleic acid, succinic acid, fumaric acid, acetic acid, formic acid, and/or propionic acid, etc. Preferred inorganic acids are hydrochloric acid and sulfuric acid. It is also possible to use acids which form an acid addition salt with the active substance or, in the case of combined preparations, with one of the active substances.

Of the organic acids, ascorbic acid, fumaric acid and citric acid are preferred, especially citric acid. If desired, mixtures of the abovementioned acids may also be used, particularly in the case of acids which have other properties in addition to their acidifying properties, e.g., those which act as flavorings or antioxidants, such as for example citric acid or ascorbic acid. Hydrochloric acid deserves special mention as a preferred inorganic acid.

If desired, pharmacologically acceptable bases may be used to titrate the pH precisely. Suitable bases include for example alkali metal hydroxides and alkali metal carbonates. The preferred alkali ion is sodium. If bases of this kind are used, care must be taken to ensure that the resulting salts, which are then contained in the finished pharmaceutical formulation, are pharmacologically compatible with the abovementioned acid.

According to the invention, there is no need to add edetic acid (EDTA) or one of the known salts thereof, sodium edetate, to the present formulation as a stabilizer or complexing agent.

Another preferred embodiment contains edetic acid and/or the salts thereof.

In a preferred embodiment with sodium edetate the content based on sodium edetate is less than 10 mg/100 ml. In this case, there is one preferred range from 5 mg/100 ml to less than 10 mg/100 ml or another from greater than 0 to 5 mg/100 ml.

In another embodiment the content of sodium edetate is 10 to 30 mg/100 ml, preferably not more than 25 mg/100 ml.

In a preferred embodiment this additive is omitted entirely.

The remarks made concerning sodium edetate also apply analogously to other comparable additives which have complexing properties and can be used instead, such as for example nitrilotriacetic acid and the salts thereof.

By complexing agents is preferably meant within the scope of the present invention molecules which are capable of entering into complex bonds. Preferably, these compounds should have the effect of complexing cations, most preferably metal cations.

The other active substances apart from the tiotropium salt in the combined preparation are selected in particular from among the antihistamines, antiallergic agents, leukotriene antagonists and/or steroids.

These active substances include:

As steroids: alclometasone, alclometasone dipropionate, alisactide, amcinonide, aminoglutethimide, aristocort diacetate, beclomethasone, beclomethasone-17,21-dipropionate, betamethasone valerate, betamethasone adamantoate, budesonide, butixocort, canesten-HC, ciclometasone, clobetasol, clobetasone, cloprednol, cloprednol, fluocortin butyl, cortivazol, deflazacort, deflazacort, demetex, deprodone, deprodone propionate, dexamethasone, dexamethasone-21-isonicotinate, dexaniethasone isonicotinate, diflorasone, difluprednate, endrisone, fluazacort, fluclorolone acetonide, flunisolide, fluocinolone acetonide, fluocinonide, fluocortin, fluocortolone caproate, fluodexan, fluorometholone, fluticasone, fluticasone propionate, formebolone, formnocortal, halcinonide, halometasone, halopredone acetate, hydrocortisone, hydrocortisone-17-butyrate, hydrocortisone aceponate, hydrocortisone butyrate propionate, icomethasone enbutate, lotrisone, mazipredone, medrysone, meprednisone, methylprednisolone aceponate, mometasone, mometasone furoate, mycophenolate mofetil, pranlukast, paramethasone acetate, prednicarbate, promedrol, seratrodast, tipredan, tixocortol pivalate, triamcinolone, triamcinolone hexacetonide, trilostane, triamcinolone benetonide, ulobetasol propionate, zileuton, and methyl 9-α-chloro-6-α-fluoro-11-β-17-α-dihydroxy-16-α-methyl-3-oxo-1,4-androstadiene-17-β-carboxylate-17-propionate.

Particularly preferred are the combinations of tiotropium bromide, or tiotropium bromide-monohydrate and budesonide, flunisolide, beclomethasone dipropionate or fluticasone, as well as the pharmacologically acceptable (possibly other) salts thereof.

The preferred combination comprises tiotropium bromide, or tiotropium bromide monohydrate and budesonide.

If the combined formulation contains a leukotriene antagonist, this is preferably selected from among montelukast, pranlukast, zafirlukast, 1-(((R)-(3-(2-(6,7-difluoro-2-quinolinyl)ethenyl)phenyl)-3-(2-(2-hydroxy-2-propyl)phenyl)thio)methylcyclopropane acetic acid, 1-(((R)-3-(3-(2-(2,3-dichlorothieno[3,2-b]pyridin-5-yl)-(E)-ethenyl)phenyl)-3-(2-(1-hydroxy-1-methylethyl)phenyl) propyl)thio)methyl)cyclopropane acetic acid or [2-[[2-(4-tert-butyl-2-thiazolyl)-5-benzofuranyl]oxymethyl]phenyl] acetic acid. Montelukast, pranlukast and/or zafirlukast are preferred.

The concentration of the leukotriene antagonist is from 0.05 wt. % to 10 wt. %, preferably up to 5 wt. %, more preferably 0.1 wt. % to 3.5 wt. %.

The following are mentioned as examples of antihistamines and antiallergic agents: azelastine, astemizole, bamipine, carbinoxamine hydrogen maleate, cetirizine, dexchlorpheniramine, chlorphenoxamine, clemastine, clemastine hydrogen fumarate, desloratadine, dimenhydrinate, dimethindene, disodium cromoglycate, diphenhydramine, doxylamine, ebastine, emedastine, epinastine, fexofenadine, ketotifen, levocabastine, loratadine, meclozine, mequitazine, mizolastine, nedocromil, pheniramine, and promethazine. Epinastine, nedocromil, disodium cromoglycate, astemizole, mequitazine, carbinoxamine, and clemastine, and the corresponding pharmaceutically acceptable salts are preferred.

In the combined preparation, the concentration of the antiallergic agents and/or antihistamines is preferably 0.05 wt. % to 15 wt. %, preferably up to 10 wt. %, more preferably 0.1 wt. % to 10 wt. %, most preferably 0.1 wt. % to 7 wt. %.

All the abovementioned active substances may optionally also be used in the form of their pharmacologically acceptable salts thereof.

The combined preparations are preferably formulations in which tiotropium is present in solution. The other active substance may be dissolved or suspended; this is generally determined by the other active substance and the particular solvent used.

If the additional active substance is one which is vulnerable at low pHs, it is preferably formulated as a suspension. The advantage of a suspended form is that the pH can be made more acidic, which is to the benefit of the stability of the dissolved tiotropium. The preferred pH range of tiotropium bromide is between 2.0 and 4.5, preferably 2.5 and 3.5, most preferably between 2.7 and 3.2.

In the case of steroids, these are preferably used in suspended form, especially fluticasone. This is particularly true if the solvent used is only water without ethanol. If ethanol is added, the steroid may also be formulated as a solution. However, it has been found that budesonide, for example, is also sufficiently stable at a pH of 3.5 if it is dissolved in a mixture of water and ethanol.

With regard to the use of the formulations according to the invention in the inhaler described within the scope of the present invention, it may be advantageous if all the ingredients of the formulation are present in solution.

As well as ethanol, other cosolvents and/or other adjuvants may be added to the formulation according to the invention.

Other preferred cosolvents are those which contain hydroxyl groups or other polar groups, for example, alcohols, especially isopropyl alcohol, glycols—especially propylene glycol, polyethylene glycol, polypropylene glycol, glycol ether, glycerol, polyoxyethylene alcohols, and polyoxyethylene fatty acid esters.

By adjuvants and additives are meant, in this context, any pharmacologically acceptable and therapeutically useful substance which is not an active substance, but can be formulated together with the active substance(s) in the pharmacologically suitable solvent, in order to improve the qualities of the active substance formulation. Preferably, these substances have no pharmacological effects or no appreciable or at least no undesirable pharmacological effects in the context of the desired therapy. The adjuvants and additives include, for example, surfactants such as, e.g., soya lecithin, oleic acid, sorbitan esters such as sorbitan trioleate, polyvinylpyrrolidone, other stabilizers, complexing agents, antioxidants and/or preservatives which prolong the shelf life of the finished pharmaceutical formulation, flavorings, vitamins and/or other additives known in the art. The additives also include pharmacologically acceptable salts such as sodium chloride, for example.

Suitable surfactants or suspension-stabilizing agents include all the pharmacologically acceptable substances which have a lipophilic hydrocarbon group and one or more functional hydrophilic groups, especially $C_{5-20}$-fatty alcohols, $C_{5-20}$-fatty acids, $C_{5-20}$-fatty acid esters, lecithin, glycerides, propyleneglycol esters, polyoxyethylenes, polysorbates, sorbitan esters and/or carbohydrates. $C_{5-20}$-fatty acids, propyleneglycol diesters and/or triglycerides and/or sorbitans of the $C_{5-20}$-fatty acids are preferred, while oleic acid and sorbitan mono-, di- or trioleates are particularly preferred. Alternatively, toxicologically and pharmaceutically acceptable polymers and/or block polymers may be used as suspension stabilizing agents.

The quantity of surfactant may be up to 1:1 based on the proportion by weight of the suspended active substances; amounts of 0.0001:1 to 0.5:1 are preferred while amounts of from 0.0001:1 to 0.25:1 are especially preferred.

The preferred excipients include antioxidants such as ascorbic acid, for example, provided that it has not already been used to adjust the pH, vitamin A, vitamin E, tocopherols and similar vitamins or provitamins occurring in the human body.

Preservatives can be added to protect the formulation from contamination with pathogenic bacteria. Suitable preservatives are those known from the prior art, particularly benzalkonium chloride or benzoic acid or benzoates, such as sodium benzoate, in the concentration known from the prior art.

Preferred formulations contain only benzalkonium chloride, an acid for adjusting the pH and sodium edetate, in addition to the solvent water and/or water/ethanol and the tiotropium salt.

In another preferred embodiment, sodium edetate is omitted. These embodiments may optionally also contain sodium chloride.

As already mentioned a number of times, tiotropium bromide is described in EP 418 716 A1 and crystalline tiotropium bromide monohydrate may be obtained using a process which is described in more detail below.

In order to prepare the crystalline monohydrate according to the present invention, the tiotropium bromide obtained by the method disclosed in EP 418 716 A1, for example, first has to be taken up in water, heated, purified with activated charcoal and, after removal of the activated charcoal, the tiotropium bromide-monohydrate is slowly crystallized while cooling slowly.

The following procedure is preferably followed:

In a reaction vessel of suitable dimensions, the solvent is mixed with tiotropium bromide, which has been obtained by the method disclosed in EP 418 716 A1, for example.

For each mole of tiotropium bromide put in, 0.4 to 1.5 kg, preferably 0.6 to 1 kg, most preferably about 0.8 kg of water are used as solvent.

The mixture obtained is heated with stirring, preferably to above 50° C., most preferably to above 60° C. The maximum temperature which can be selected is determined by the boiling point of the solvent used. Preferably, the mixture is heated to a range from 80° C. to 90° C. Activated charcoal, either dry or moistened with water, is added to this solution. Preferably, 10 g to 50 g, more preferably 15 g to 35 g, most preferably about 25 g of activated charcoal are put in per mol of tiotropium bromide used. If desired the activated charcoal is suspended in water before being added to the solution containing tiotropium bromide. 70 g to 200 g, preferably 100 g to 160 g, more preferably about 135 g of water are used, per mol of tiotropium bromide put in, in order to suspend the activated charcoal. If the activated charcoal is suspended in water beforehand, before being added to the solution containing tiotropium bromide, it is advisable to rinse again with the same amount of water. After the activated charcoal has been added, stirring is continued at constant temperature for between 5 minutes and 60 minutes, preferably between 10 minutes and 30 minutes, more preferably for about 15 minutes and the mixture obtained is filtered to remove the activated charcoal. The filter is then rinsed with water. 140 g to 400 g, preferably 200 g to 320 g, most preferably about 270 g of water are used for this, per mol of tiotropium bromide used. The filtrate is then slowly cooled, preferably to a temperature of 20° C. to 25° C. The cooling preferably takes place at a cooling rate of 1 to 10° C. every 10 to 30 minutes, preferably 2° C. to 8° C. every 10 to 30 minutes, more preferably 3° C. to 5° C. every 10 to 20 minutes, most preferably 3° C. to 5° C. about every 20 minutes. If desired the cooling to 20° C. to 25° C. may be followed by further cooling to below 20° C., more preferably to 10° C. to 15° C. After cooling is complete, stirring is continued for between 20 minutes and 3 hours, preferably between 40 minutes and 2 hours, more preferably for about one hour to complete the crystallization. The crystals obtained are then isolated by filtering or suction filtering to remove the solvent. If it should prove necessary to subject the crystals obtained to a further washing step, it is advisable to use water or acetone as the washing solvent. 0.1 L to 1.0 L, preferably 0.2 L to 0.5 L, more preferably about 0.3 L of solvent may be used per mol of tiotropium bromide put in, in order to wash the tiotropium bromide monohydrate crystals obtained. If necessary the washing step may be repeated. The product obtained is dried in vacuo or using circulating heated air until a water content of 2.5% to 4.0% is obtained.

According to one aspect the present invention therefore also relates to formulations of solutions of the type described above using crystalline tiotropium bromide monohydrate which may be obtained by the procedure described above.

The pharmaceutical formulations containing tiotropium salts according to the invention are preferably used in an inhaler of the kind described hereinbefore in order to produce the propellant-free aerosols according to the invention. At this point we should once again expressly mention the patent documents described hereinbefore, to which reference is hereby made.

As described at the beginning, a further developed embodiment of the preferred inhaler is disclosed in WO 97/12687 and FIG. 6 thereof. This nebulizer (RESPIMAT®) can advantageously be used to produce the inhalable aerosols according to the invention containing a tiotropium salt as active substance. Because of its cylindrical shape and handy size of less than 9 cm to 15 cm long and 2 cm to 4 cm wide, the device can be carried anywhere by the patient. The nebulizer sprays a defined volume of the pharmaceutical formulation out through small nozzles at high pressures, so as to produce inhalable aerosols.

The preferred atomizer essentially consists of an upper housing part, a pump housing, a nozzle, a locking clamp, a spring housing, a spring and a storage container, characterized by

- a pump housing fixed in the upper housing part and carrying at one end a nozzle body with the nozzle or nozzle arrangement,
- a hollow piston with valve body,
- a power take-off flange in which the hollow body is fixed and which is located in the upper housing part,
- a locking clamping mechanism located in the upper housing part,
- a spring housing with the spring located therein, which is rotatably mounted on the upper housing part by means of a rotary bearing,
- a lower housing part which is fitted onto the spring housing in the axial direction.

The hollow piston with valve body corresponds to a device disclosed in WO 97/12687. It projects partially into the cylinder of the pump housing and is disposed to be axially movable in the cylinder. Reference is made particularly to FIGS. 1 to 4, especially FIG. 3, and the associated parts of the description. At the moment of release of the spring the hollow piston with valve body exerts, at its high pressure end, a pressure of 5 MPa to 60 MPa (about 50 to 600 bar), preferably 10 MPa to 60 MPa (about 100 to 600 bar) on the fluid, the measured amount of active substance solution. Volumes of 10 to 50 microliters are preferred, volumes of 10 to 20 microliters are more preferable, whilst a volume of 15 microliters per actuation is particularly preferred.

The valve body is preferably mounted at the end of the hollow piston which faces the nozzle body.

The nozzle in the nozzle body is preferably microstructured, i.e., produced by micro-engineering. Microstructured nozzle bodies are disclosed for example in WO 94/07607; reference is hereby made to the contents of this specification, especially FIG. 1 and the associated description, and which is incorporated herein by reference in its entirety.

The nozzle body consists for example of two sheets of glass and/or silicon securely fixed together, at least one of which has one or more microstructured channels which connect the nozzle inlet end to the nozzle outlet end. At the nozzle outlet end there is at least one round or non-round opening 2 microns to 10 microns deep and 5 microns to 15 microns wide, the depth preferably being 4.5 microns to 6.5 microns and the length being 7 microns to 9 microns.

If there are a plurality of nozzle openings, preferably two, the directions of spraying of the nozzles in the nozzle body may run parallel to each other or may be inclined relative to one another in the direction of the nozzle opening. In the case of a nozzle body having at least two nozzle openings at the outlet end, the directions of spraying may be inclined relative to one another at an angle of 20° to 160°, preferably at an angle of 60° to 150°, most preferably 80° to 100°.

The nozzle openings are preferably arranged at a spacing of 10 microns to 200 microns, more preferably at a spacing of 10 microns to 100 microns, still more preferably 30 microns to 70 microns. A spacing of 50 microns is most preferred.

The directions of spraying therefore meet in the region of the nozzle openings.

As already mentioned, the liquid pharmaceutical preparation hits the nozzle body at an entry pressure of up to 600 bar, preferably 200 bar to 300 bar and is atomized through the nozzle openings into an inhalable aerosol. The preferred particle sizes of the aerosol are up to 20 microns, preferably 3 microns to 10 microns.

The locking clamping mechanism contains a spring, preferably a cylindrical helical compression spring as a store for the mechanical energy. The spring acts on the power take-off flange as a spring member the movement of which is determined by the position of a locking member. The travel of the power take-off flange is precisely limited by an upper stop and a lower stop. The spring is preferably tensioned via a stepping-up gear, e.g., a helical sliding gear, by an external torque which is generated when the upper housing part is turned relative to the spring housing in the lower housing part. In this case, the upper housing part and the power take-off flange contain a single- or multi-speed spline gear.

The locking member with the engaging locking surfaces is arranged in an annular configuration around the power take-off flange. It consists for example of a ring of plastics or metal which is inherently radially elastically deformable. The ring is arranged in a plane perpendicular to the axis of the atomizer. After the locking of the spring, the locking surfaces of the locking member slide into the path of the power take-off flange and prevent the spring from being released. The locking member is actuated by means of a button. The actuating button is connected or coupled to the locking member. In order to actuate the locking clamping mechanism the actuating button is moved parallel to the annular plane, preferably into the atomizer, and the deformable ring is thereby deformed in the annular plane. Details of the construction of the locking clamping mechanism are described in WO 97/20590.

The lower housing part is pushed axially over the spring housing and covers the bearing, the drive for the spindle and the storage container for the fluid.

When the atomizer is operated, the upper part of the housing is rotated relative to the lower part, the lower part taking the spring housing with it. The spring meanwhile is compressed and biased by means of the helical sliding gear, and the clamping mechanism engages automatically. The angle of rotation is preferably a whole-number fraction of 360°, e.g., 180°. At the same time as the spring is tensioned, the power take-off component in the upper housing part is moved along by a given amount, the hollow piston is pulled back inside the cylinder in the pump housing, as a result of which some of the fluid from the storage container is sucked into the high pressure chamber in front of the nozzle.

If desired, a plurality of replaceable storage containers containing the fluid to be atomized can be inserted in the atomizer one after another and then used. The storage container contains the aqueous aerosol preparation according to the invention.

The atomizing process is initiated by gently pressing the actuating button. The clamping mechanism then opens the way for the power take-off component. The biased spring pushes the piston into the cylinder in the pump housing. The fluid emerges from the nozzle of the atomizer in the form of a spray.

Further details of the construction are disclosed in PCT applications WO 97/12687 and WO 97/20590, to which reference is hereby made and each of which is incorporated herein by reference in their entireties.

The components of the atomizer (nebulizer) are made of a material suitable for their function. The housing of the atomizer and, if the function allows, other parts as well are preferably made of plastics, e.g., by injection moulding. For medical applications, physiologically acceptable materials are used.

FIGS. 1a/b, which are identical to FIGS. 6a/b of WO 97/12687, show the RESPIMAT® nebulizer with which the aqueous aerosol preparations according to the invention can advantageously be inhaled.

FIG. 1a shows a longitudinal section through the atomizer with the spring under tension, and FIG. 1b shows a longitudinal section through the atomizer with the spring released.

The upper housing part (51) contains the pump housing (52), on the end of which is mounted the holder (53) for the atomizer nozzle. In the holder is the nozzle body (54) and a filter (55). The hollow piston (57) fixed in the power take-off flange (56) of the locking clamping mechanism projects partly into the cylinder of the pump housing. At its end the hollow piston carries the valve body (58). The hollow piston is sealed off by the gasket (59). Inside the upper housing part is the stop (60) on which the power take-off flange rests when the spring is relaxed. Located on the power take-off flange is the stop (61) on which the power take-off flange rests when the spring is under tension. After the tensioning of the spring, the locking member (62) slides between the stop (61) and a support (63) in the upper housing part. The actuating button (64) is connected to the locking member. The upper housing part ends in the mouthpiece (65) and is closed off by the removable protective cap (66).

The spring housing (67) with compression spring (68) is rotatably mounted on the upper housing part by means of the snap-fit lugs (69) and rotary bearings. The lower housing part (70) is pushed over the spring housing. Inside the spring housing is the replaceable storage container (71) for the fluid (72) which is to be atomized. The storage container is closed off by the stopper (73), through which the hollow piston projects into the storage container and dips its end into the fluid (supply of active substance solution).

The spindle (74) for the mechanical counter is mounted on the outside of the spring housing. The drive pinion (75) is located at the end of the spindle facing the upper housing part. On the spindle is the slider (76).

The nebulizer described above is suitable for nebulizing the aerosol preparations according to the invention to form an aerosol suitable for inhalation.

If the formulation according to the invention is nebulized using the method described above (RESPIMAT®), the mass expelled, in at least 97%, preferably at least 98% of all the actuations of the inhaler (puffs), should correspond to a defined quantity with a range of tolerance of not more than 25%, preferably 20% of this quantity. Preferably, between 5 mg and 30 mg, more preferably between 5 mg and 20 mg of formulation are delivered as a defined mass per puff.

The proportion of the mass delivered which is outside a tolerance limit of not more than 25% in relation to the desired mass should be less than 1.5%, preferably less than 1.2%.

However, the formulation according to the invention can also be nebulized using inhalers other than those described above, for example jet-stream inhalers.

EXAMPLES

I. Example of the Synthesis of Tiotropium Bromide Monohydrate 15.0 kg of tiotropium bromide are added to 25.7 kg of water in a suitable reaction vessel. The mixture is heated to 80° C. to 90° C. and stirred at constant temperature until a clear solution is formed. Activated charcoal (0.8 kg), moistened with water, is suspended in 4.4 kg of water, this mixture is added to the solution containing tiotropium bromide and rinsed with 4.3 kg of water. The mixture thus obtained is stirred for at least 15 minutes at 80° C. to 90° C. and then filtered through a heated filter into an apparatus which has been preheated to an outer temperature of 70° C. The filter is rinsed with 8.6 kg of water. The contents of the apparatus are cooled to a temperature of 20° C. to 25° C. at a rate of 3° C. to 5° C. every 20 minutes. Using cold water, the apparatus is cooled further to 10° C. to 15° C. and crystallization is completed by stirring for at least another hour. The crystals are isolated using a suction filter drier, the crystal slurry isolated is washed with 9 L of cold water (10° C. to 15° C.) and cold acetone (10° C. to 15° C.). The crystals obtained are dried at 25° C. for 2 hours in a nitrogen current. Yield: 13.4 kg of tiotropium bromide monohydrate (86% of theory).

II. Examples of Formulations

TABLE I

Pharmaceutical Formulations
100 g of Pharmaceutical Preparation Contains the Following

| Example No. | Tiotropium Bromide (Based on Tiotropium) (g) | Tiotropium Bromide Monohydrate (Based on Tiotropium) (g) | Benzalkonium Chloride (mg) | Sodium Edetate (mg) | pH, Adjusted with HCl (1 N) |
|---|---|---|---|---|---|
| 1 | 0.099 | — | 10 | 25 | 3.0 |
| 2 | 0.006 | — | 10 | 25 | 3.0 |
| 3 | 0.099 | — | 10 | 10 | 3.0 |
| 4 | 0.006 | — | 10 | 10 | 3.0 |
| 5 | — | 0.099 | 10 | 25 | 3.0 |
| 6 | — | 0.006 | 10 | 25 | 3.0 |
| 7 | — | 0.099 | 10 | 10 | 3.0 |
| 8 | — | 0.006 | 10 | 10 | 3.0 |

Note: The remainder of the pharmaceutical formulation is water or water/ethanol and one of the above-mentioned active substances in an amount known from the prior art.

Examples 9 to 12.

Budesonide

Each of Examples 1 to 8 may additionally contain:

Example 9a: budesonide: 0.3 g, pH, adjusted with HCl:3.0, solvent water only, no ethanol;

Example 9b: budesonide: 0.3 g, pH, adjusted with HCl:3,5;

Example 9c: budesonide: 0.3 g, pH, adjusted with HCl:4.0;

Example 10: analogous to Example 9a to 9c with budesonide: 0.6 g,

Example 11: analogous to Example 9a to 9c with budesonide: 1.3 g,

Example 12: analogous to Example 9a to 9c with budesonide: 2.0 g.

In Examples 9 to 12 the steroid is present in the formulation in suspension. Sorbitan trioleate may be used as a surfactant.

Examples 13 to 15

Analogous to Examples 9 to 12. Benzalkonium chloride is exchanged for sodium benzoate.

Examples 16 to 19

Analogous to Examples 9 to 12. Instead of hydrochloric acid, citric acid is exclusively used to adjust the pH.

Examples 20 to 30

The ingredients and amounts are analogous to Examples 9 to 19. Instead of water, a mixture of water (10 vol. %) and ethanol (90 vol. %) is used. Budesonide is present in solution.

Example 31

Epinastine: 0.2 g;

EDTA: 25 mg;

Tiotropium bromide monohydrate: 29 mg;

0.1 N hydrochloric acid to adjust the pH to 3.0; and water to 100 ml.

Other Examples

Analogously to Examples 9 to 30 described above, the same amount of flunisolide, beclomethasone dipropionate, or fluticasone is used instead of budesonide. In the case of fluticasone, lecithin is preferably added instead of sorbitan trioleate in the case of the suspension formulation. The steroids are formulation as a suspension if the solvent used is water on its own. In the case of a mixture of water and ethanol, the steroid may be in solution.

We claim:

1. A liquid, propellant-free pharmaceutical preparation comprising:

(a) a first active substance comprising a tiotropium salt, in a concentration based on tiotropium of between 0.0005% and 5% by weight;

(b) a second active substance selected from the group consisting of: an antiallergic, antihistamine, steroid, and leukotriene antagonist;

(c) a solvent selected from water or a water/ethanol mixture; and (d) a pharmacologically acceptable preservative, wherein the pH of the preparation is adjusted to between 2.0 and 4.5 with an acid and the tiotropium salt is dissolved in the solvent, optionally including a pharmacologically acceptable complexing agent, stabilizer, a pharmacologically acceptable cosolvent, or other pharmacologically acceptable adjuvants and additives.

2. The pharmaceutical preparation according to claim 1, wherein the tiotropium salt is a salt formed with HBr, HCl, HI, monomethylsulfuric acid ester, methanesulfonic acid, or-p-toluenesulfonic acid.

3. The pharmaceutical preparation according to claim 1, wherein the active substance is tiotropium bromide.

4. The pharmaceutical preparation according to claim 1, wherein the active substance is tiotropium bromide monohydrate.

5. The pharmaceutical preparation according to claim 1, wherein the solvent is water.

6. The pharmaceutical preparation according to claim 2, wherein the solvent is water.

7. The pharmaceutical preparation according to claim 3, wherein the solvent is water.

8. The pharmaceutical preparation according to claim 4, wherein the solvent is water.

9. The pharmaceutical preparation according to claim 1, wherein the solvent is a water-ethanol mixture with up to 90 vol. % of ethanol.

10. The pharmaceutical preparation according to claim 2, wherein the solvent is a water-ethanol mixture with up to 90 vol. % of ethanol.

11. The pharmaceutical preparation according to claim 3, wherein the solvent is a water-ethanol mixture with up to 90 vol. % of ethanol.

12. The pharmaceutical preparation according to claim 4, wherein the solvent is a water-ethanol mixture with up to 90 vol. % of ethanol.

13. The pharmaceutical preparation according to claim 9, wherein the solvent is a water-ethanol mixture with up to 70 vol. % of ethanol.

14. The pharmaceutical preparation according to claim 13, wherein the solvent is a water-ethanol mixture with up to 30 vol. % of ethanol.

15. The pharmaceutical preparation according to one of claims 1 to 4, wherein the pharmaceutical preparation does not contain a complexing agent.

16. The pharmaceutical preparation according to one of claims 1 to 4, wherein the pharmaceutical preparation does not contain a stabilizer.

17. The pharmaceutical preparation according to one of claims 1 to 4, wherein edetic acid salt is present in an amount of greater than 0 up to 25 mg/100 ml.

18. The pharmaceutical preparation according to claim 17, wherein edetic acid salt is present in an amount of from 5 to less than 10 mg/100 ml.

19. The pharmaceutical preparation according to claim 17, wherein the edetic acid salt is sodium edetate.

20. The pharmaceutical preparation according to one of claims 1 to 4, wherein the pH is between 2.5 and 3.5.

21. The pharmaceutical preparation according to claim 20, wherein the pH is between 2.7 and 3.3.

22. The pharmaceutical preparation according to claim 21, wherein the pH is between 2.7 and 3.0.

23. The pharmaceutical preparation according to one of claims 1 to 4, wherein the concentration based on tiotropium is between 0.0005% and 5% by weight.

24. The pharmaceutical preparation according to claim 23, wherein the concentration based on tiotropium is between 0.001% to 3% by weight.

25. The pharmaceutical preparation according to one of claims 1 to 4, wherein the pharmacologically acceptable preservative is benzalkonium chloride.

26. The pharmaceutical preparation according to one of claims 1 to 4, wherein the pharmaceutical preparation comprises a pharmacologically acceptable adjuvant or additive.

27. The pharmaceutical preparation according to claim 26, wherein pharmacologically acceptable adjuvant or additive is an antioxidant.

28. The pharmaceutical preparation according to one of claims 1 to 4, wherein the pharmaceutical preparation contains no cosolvents and/or pharmacologically acceptable adjuvants and additives apart from the preservative.

29. The pharmaceutical preparation according to one of claims 1 to 4, wherein the tiotropium salt is present in a concentration based on tiotropium of between 0.001% and 3% by weight.

30. The pharmaceutical preparation according to one of claims 1 to 4, wherein the tiotropium salt is present in a concentration based on tiotropium of between 0.001 % and 0.1 % by weight.

31. The pharmaceutical preparation according to one of claims 1 to 4, wherein the ingredients are dissolved in the solvent.

32. The pharmaceutical preparation according to one of claims 1 to 4, wherein the second active substance is in suspension in the solvent.

33. The pharmaceutical preparation according to one of claims 1 to 4, wherein the second active substance is a steroid.

34. The pharmaceutical preparation according to claim 33, wherein the concentration of the steroid is 0.05 wt. % to 5 wt. %.

35. The pharmaceutical preparation according to claim 33, wherein the steroid is selected from the group consisting of: budesonide, beclomethasone dipropionate, fluticasone, and flunisolide.

36. The pharmaceutical preparation according to one of claims 1 to 4, wherein the second active substance is an antiallergic or an antihistamine.

37. The pharmaceutical preparation according to claim 36, wherein the concentration of the antiallergic or the antihistamine is 0.05 wt. % to 15 wt. %.

38. The pharmaceutical preparation according to claim 36, wherein the antiallergic or the antihistamine is selected from the group consisting of: epinastine, nedocromil, disodium cromoglycate, astemizole, mequitazine, carbinoxamine, and clemastine, or a corresponding pharmaceutically acceptable salt thereof.

39. The pharmaceutical preparation according to one of claims 1 to 4, wherein the second active substance is a leukotriene antagonist.

40. The pharmaceutical preparation according to claim 39, wherein the concentration of the leukotriene antagonist is 0.05 wt. % to 10 wt. %.

41. The pharmaceutical preparation according to claim 39, wherein the leukotriene antagonist is selected from the group consisting of: montelukast, pranlukast, zafirlukast, 1-(((R)-(3-(2-(6,7-difluoro-2-quinolinyl)ethenyl)phenyl)-3-(2-(2-hydroxy-2-propyl)phenyl)thio)methylcyclopropaneacetic acid, and 1-(((R)-3-(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid, [2-[[2-(4-tert-butyl-2-thiazolyl)-5-benzofuranyl]oxymethyl]phenyl]acetic acid.

42. A pharmaceutical preparation according to claim 1, wherein the pharmaceutical preparation comprises: water as the solvent; a surfactant; 0.1 wt. % of tiotropium bromide; a second active substance selected from the group consisting of: antiallergics, antihistamines, steroids, and leukotriene antagonists; 0.01 wt. % of benzalkonium chloride; and 0.05 wt. % of sodium edetate, wherein the pH of the preparation is adjusted to 3.0 with hydrochloric acid or citric acid.

43. A method for administering a pharmaceutical preparation according to one of claims 1 to 4, comprising nebulizing the pharmaceutical preparation in an inhaler selected from the group consisting of an inhaler according to FIGS. Ia or Ib.

44. A method for administering a pharmaceutical preparation according to one of claims 1 to 4, comprising nebulizing the pharmaceutical preparation in an inhaler which nebulizes defined amounts of the pharmaceutical preparation by the application of pressures from 100 to 600 bar through a nozzle having at least one nozzle opening with a depth of 2 to 10 microns and a width of 5 to 15 microns to form an inhalable aerosol.

45. The method according to claim 44, wherein at least one nozzle opening is at least two nozzle openings which are inclined relative to one another in the direction of the nozzle opening at an angle of from 20 degrees to 160 degrees.

46. The method according to claim 44, wherein the defined amounts of the pharmaceutical preparation are 10 to 50 microliters.

47. The method according to claim 43, wherein the inhaler is 9 cm to 15 cm long and 2 cm to 4 cm wide.

48. The method according to claim 44, wherein the inhaler is 9 cm to 15 cm long and 2 cm to 4 cm wide.

49. The method according to claim 43, wherein the mass of pharmaceutical formulation delivered in at least 97% of all actuations of the inhaler is between 5 mg and 30 mg within a range of tolerance of 25%.

50. The method according to claim 44, wherein the mass of pharmaceutical formulation delivered in at least 97% of all actuations of the inhaler is between 5 mg and 30 mg within a range of tolerance of 25%.

51. The method according to claim 43, wherein the mass of pharmaceutical formulation delivered in at least 97% of all actuations of the inhaler is between 5 mg and 30 mg within a range of tolerance of 20%.

52. The method according to claim 44, wherein the mass of pharmaceutical formulation delivered in at least 97% of all actuations of the inhaler is between 5 mg and 30 mg within a range of tolerance of 20%.

53. The method according to claim 43, wherein the mass of pharmaceutical formulation delivered in at least 98% of all actuations of the inhaler is between 5 mg and 30 mg within a range of tolerance of 20%.

54. The method according to claim 44, wherein the mass of pharmaceutical formulation delivered in at least 98% of all actuations of the inhaler is between 5 mg and 30 mg within a range of tolerance of 20%.

55. A method of treating asthma or COPD in a patient, the method comprising administering to the patient a pharmaceutical preparation according to one of claims 1 to 4.

56. A method of treating asthma or COPD in a patient, the method comprising administering to the patient a pharmaceutical preparation using the method of claim 43.

57. A method of treating asthma or COPD in a patient, the method comprising administering to the patient a pharmaceutical preparation using the method of claim 44.

58. A method for administering a pharmaceutical preparation according to claim 26, comprising nebulizing the pharmaceutical preparation in an inhaler selected from the group consisting of an inhaler according to FIGS. Ia or Ib.

59. A method for administering a pharmaceutical preparation according to claim 26, comprising nebulizing the pharmaceutical preparation in an inhaler which nebulizes defined amounts of the pharmaceutical preparation by the application of pressures from 100 to 600 bar through a nozzle having at least one nozzle opening with a depth of 2 to 10 microns and a width of 5 to 15 microns to form an inhalable aerosol.

60. A method for administering a pharmaceutical preparation according to claim 28, comprising nebulizing the pharmaceutical preparation in an inhaler selected from the group consisting of an inhaler according to FIGS. Ia or Ib.

61. A method for administering a pharmaceutical preparation according to claim 28, comprising nebulizing the pharmaceutical preparation in an inhaler which nebulizes defined amounts of the pharmaceutical preparation by the application of pressures from 100 to 600 bar through a nozzle having at least one nozzle opening with a depth of 2 to 10 microns and a width of 5 to 15 microns to form an inhalable aerosol.

62. A method for administering a pharmaceutical preparation according to claim 33, comprising nebulizing the pharmaceutical preparation in an inhaler selected from the group consisting of an inhaler according to FIGS. Ia or Ib.

63. A method for administering a pharmaceutical preparation according to claim 33, comprising nebulizing the pharmaceutical preparation in an inhaler which nebulizes defined amounts of the pharmaceutical preparation by the application of pressures from 100 to 600 bar through a nozzle having at least one nozzle opening with a depth of 2 to 10 microns and a width of 5 to 15 microns to form an inhalable aerosol.

64. A method for administering a pharmaceutical preparation according to claim 36, comprising nebulizing the pharmaceutical preparation in an inhaler selected from the group consisting of an inhaler according to FIGS. Ia or Ib.

65. A method for administering a pharmaceutical preparation according to claim 36, comprising nebulizing the pharmaceutical preparation in an inhaler which nebulizes defined amounts of the pharmaceutical preparation by the application of pressures from 100 to 600 bar through a nozzle having at least one nozzle opening with a depth of 2 to 10 microns and a width of 5 to 15 microns to form an inhalable aerosol.

66. A method for administering a pharmaceutical preparation according to claim 39, comprising nebulizing the pharmaceutical preparation in an inhaler selected from the group consisting of an inhaler according to FIGS. Ia or Ib.

67. A method for administering a pharmaceutical preparation according to claim 39, comprising nebulizing the pharmaceutical preparation in an inhaler which nebulizes defined amounts of the pharmaceutical preparation by the application of pressures from 100 to 600 bar through a nozzle having at least one nozzle opening with a depth of 2 to 10 microns and a width of 5 to 15 microns to form an inhalable aerosol.

68. A method for administering a pharmaceutical preparation according to claim 41, comprising nebulizing the pharmaceutical preparation in an inhaler selected from the group consisting of an inhaler according to FIGS. Ia or Ib.

69. A method for administering a pharmaceutical preparation according to claim 41, comprising nebulizing the pharmaceutical preparation in an inhaler which nebulizes defined amounts of the pharmaceutical preparation by the application of pressures from 100 to 600 bar through a nozzle having at least one nozzle opening with a depth of 2 to 10 microns and a width of 5 to 15 microns to form an inhalable aerosol.

70. A method of treating asthma or COPD in a patient, the method comprising administering to the patient a pharmaceutical preparation using the method of claim 58.

71. A method of treating asthma or COPD in a patient, the method comprising administering to the patient a pharmaceutical preparation using the method of claim 59.

72. A method of treating asthma or COPD in a patient, the method comprising administering to the patient a pharmaceutical preparation using the method of claim 60.

73. A method of treating asthma or COPD in a patient, the method comprising administering to the patient a pharmaceutical preparation using the method of claim 61.

74. A method of treating asthma or COPD in a patient, the method comprising administering to the patient a pharmaceutical preparation using the method of claim 62.

75. A method of treating asthma or COPD in a patient, the method comprising administering to the patient a pharmaceutical preparation using the method of claim 63.

76. A method of treating asthma or COPD in a patient, the method comprising administering to the patient a pharmaceutical preparation using the method of claim 64.

77. A method of treating asthma or COPD in a patient, the method comprising administering to the patient a pharmaceutical preparation using the method of claim 65.

78. A method of treating asthma or COPD in a patient, the method comprising administering to the patient a pharmaceutical preparation using the method of claim 66.

79. A method of treating asthma or COPD in a patient, the method comprising administering to the patient a pharmaceutical preparation using the method of claim 67.

80. A method of treating asthma or COPD in a patient, the method comprising administering to the patient a pharmaceutical preparation using the method of claim 68.

81. method of treating asthma or COPD in a patient, the method comprising administering to the patient a pharmaceutical preparation using the method of claim 69.

* * * * *

UNITED STATES PATENT AND TRADEMARK OFFICE
CERTIFICATE OF CORRECTION

| | |
|---|---|
| PATENT NO. | : 6,890,517 B2 |
| APPLICATION NO. | : 10/395777 |
| DATED | : May 10, 2005 |
| INVENTOR(S) | : Karin Drechsel et al. |

It is certified that error appears in the above-identified patent and that said Letters Patent is hereby corrected as shown below:

In Column 12, line 57, Cancel Claim 2

In Column 13, line 1, Cancel Claim 6

In Column 13, line 10, Cancel Claim 10

In Column 13, lines 25-67, Claims 15, 16, 17, 20, 23, 25, 26, 28, and 29, and in Column 14, lines 1-67, Claims 30, 31, 32, 33, 36, 39, 43, and 44, and in Column 15, lines 38-40, Claim 55; delete - according to one of claims 1 to 4 - and insert --according to any one of claims 1,3 or 4--.

Signed and Sealed this

Twenty-eighth Day of August, 2007

JON W. DUDAS
*Director of the United States Patent and Trademark Office*